(12) United States Patent
Hashmi et al.

(10) Patent No.: US 8,586,738 B2
(45) Date of Patent: Nov. 19, 2013

(54) PROCESS FOR THE PREPARATION OF VALGANCICLOVIR HYDROCHLORIDE

(75) Inventors: Mohammed Salman Hashmi, Aligarh (IN); Mukesh Kumar Sharma, Gurgaon (IN); Chandra Has Khanduri, Gurgaon (IN)

(73) Assignee: Ranbaxy Laboratories Limited

( * ) Notice: Subject to any disclaimer, the term of this patent is extended or adjusted under 35 U.S.C. 154(b) by 0 days.

(21) Appl. No.: 13/390,756

(22) PCT Filed: Aug. 12, 2010

(86) PCT No.: PCT/IB2010/053657
§ 371 (c)(1),
(2), (4) Date: Mar. 30, 2012

(87) PCT Pub. No.: WO2011/018771
PCT Pub. Date: Feb. 17, 2011

(65) Prior Publication Data
US 2012/0190850 A1    Jul. 26, 2012

(30) Foreign Application Priority Data
Aug. 12, 2009  (IN) .......................... 1683/DEL/2009

(51) Int. Cl.
*C07D 473/00*        (2006.01)

(52) U.S. Cl.
USPC ........................................ 544/276

(58) Field of Classification Search
USPC ........................................ 544/276
See application file for complete search history.

(56) References Cited

U.S. PATENT DOCUMENTS

| | | | |
|---|---|---|---|
| 6,083,953 A | 7/2000 | Nestor et al. | 514/262 |
| 6,340,756 B1 | 1/2002 | Dvorak et al. | 544/276 |

FOREIGN PATENT DOCUMENTS

| | | | |
|---|---|---|---|
| WO | WO 97/27196 | 7/1997 | C07D 473/18 |
| WO | WO 2005/092891 | 10/2005 | C07D 473/00 |

OTHER PUBLICATIONS

Benoiton, "On the side-reaction of N-alkylation of amino groups during hydrogenolytic deprotection in alcohol-containing solvents", *International Journal of Peptide & Protein Research*, 41:611 (1993).
Greene and Wuts, 1999. *Protective Groups in Organic Synthesis*. 3rd ed. New York:John Wiley and Sons, 531-535.
Yan-ping et al., "Synthesis of anti-viral agent valganciclovir", *Chinese Journal of Antibiotics*, 30:336-337 and 353 (2005).

*Primary Examiner* — Noble Jarrell
*Assistant Examiner* — Laura Daniel

(57) ABSTRACT

The present invention provides a novel process for the preparation of pure valganciclovir hydrochloride.

13 Claims, 3 Drawing Sheets

FIG. 2A

Peak Results

| Name | Retention Time (min) | Area (µV*sec) | % Area | RT Ratio | Int Type | Result # |
|---|---|---|---|---|---|---|
| Peak1 | 2.19 | 391 | 0.00 | 0.27 | BB | 1 |
| Peak2 | 2.92 | 641 | 0.01 | 0.37 | VV | 1 |
| Peak3 | 2.99 | 569 | 0.01 | 0.37 | VB | 1 |
| Peak4 | 3.25 | 3649 | 0.05 | 0.41 | BB | 1 |
| Peak5 | 4.03 | 1015 | 0.01 | 0.50 | BB | 1 |
| Peak6 | 4.39 | 979 | 0.01 | 0.55 | BB | 1 |
| Peak7 | 6.93 | 4537915 | 57.32 | 0.87 | BB | 1 |
| Peak8 | 7.99 | 3358808 | 42.42 |  | BB | 1 |
| Peak9 | 11.09 | 646 | 0.01 | 1.39 | BB | 1 |
| Peak10 | 11.54 | 767 | 0.01 | 1.44 | BB | 1 |
| Peak11 | 12.15 | 569 | 0.01 | 1.52 | BB | 1 |
| Peak12 | 12.68 | 443 | 0.01 | 1.59 | VV | 1 |
| Peak13 | 12.94 | 736 | 0.01 | 1.62 | VV | 1 |
| Peak14 | 13.17 | 1596 | 0.02 | 1.65 | VB | 1 |
| Peak15 | 13.47 | 685 | 0.01 | 1.68 | BV | 1 |
| Peak16 | 13.73 | 740 | 0.01 | 1.72 | VB | 1 |
| Peak17 | 14.12 | 275 | 0.00 | 1.77 | BB | 1 |
| Peak18 | 14.40 | 948 | 0.01 | 1.80 | BB | 1 |
| Peak19 | 16.14 | 910 | 0.01 | 2.02 | BB | 1 |
| Peak20 | 17.27 | 398 | 0.01 | 2.16 | BB | 1 |
| Peak21 | 18.16 | 1474 | 0.02 | 2.27 | BB | 1 |
| Peak22 | 18.87 | 413 | 0.01 | 2.36 | BB | 1 |
| Peak23 | 19.90 | 467 | 0.01 | 2.49 | BB | 1 |
| Peak24 | 20.16 | 620 | 0.01 | 2.52 | BB | 1 |
| Peak25 | 20.43 | 921 | 0.01 | 2.56 | BB | 1 |
| Peak26 | 20.87 | 639 | 0.01 | 2.61 | BB | 1 |

PROCESS FOR THE PREPARATION OF VALGANCICLOVIR HYDROCHLORIDE

FIELD OF THE INVENTION

The present invention provides a process for the preparation of pure valganciclovir hydrochloride.

BACKGROUND OF THE INVENTION

Valganciclovir hydrochloride is chemically, L-valine, 2-[(2-amino-1,6-dihydro-6-oxo-9H-purin-9-yl)-methoxy]-3-hydroxypropanyl ester, monohydrochloride, having the structure as represented by Formula I.

FORMULA I

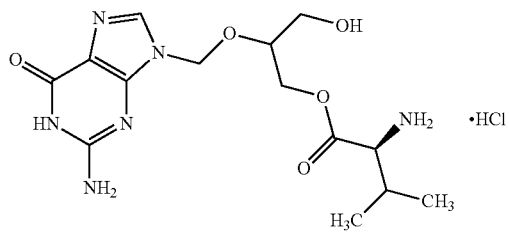

It is the hydrochloride salt of mono-L-valyl ester prodrug of antiviral compound ganciclovir of Formula II.

FORMULA II

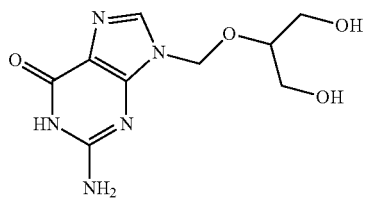

Valganciclovir hydrochloride is marketed in the United States under the brand name Valcyte® for the treatment of cytomegalovirus retinitis in patients with acquired immunodeficiency syndrome and for the prevention of cytomegalovirus disease in kidney, heart, and kidney-pancreas transplant patients at high risk.

Several methods for the preparation of valganciclovir hydrochloride are reported in literature such as those described in U.S. Pat. Nos. 6,083,953; 6,340,756; and WO 2005/092891, which are incorporated herein by reference.

The processes described in the literature involve preparation of valganciclovir by the deprotection of mono-benzyloxycarbonyl-L-valine ganciclovir of Formula III

FORMULA III

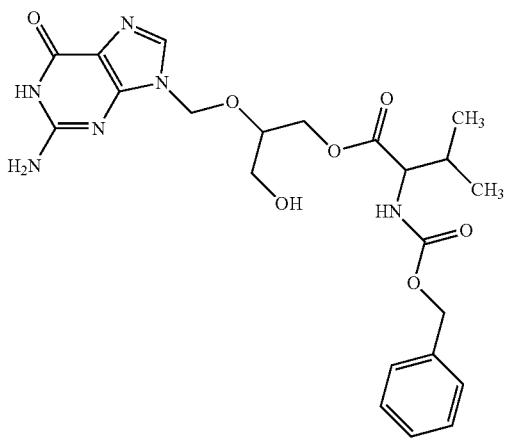

in methanol or ethanol.

The present inventors have observed that when deprotection of mono-benzyloxycarbonyl-L-valine ganciclovir of Formula III is carried out using methanol or ethanol, N-methyl valganciclovir and N-ethyl valganciclovir impurities are formed along with valganciclovir hydrochloride. United States Pharmacopoeia (USP) for valganciclovir hydrochloride requires N-methyl valganciclovir impurity to be controlled within a limit of not more than 0.3% in valganciclovir hydrochloride.

SUMMARY OF THE INVENTION

The present inventors have developed a process for the preparation of valganciclovir hydrochloride which avoids the formation of N-alkyl valganciclovir impurities.

A first aspect of the present invention provides a process for the preparation of valganciclovir hydrochloride of Formula I,

FORMULA I

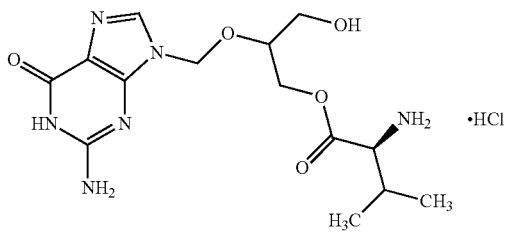

comprising deprotection of mono-protected ganciclovir of Formula IV,

FORMULA IV

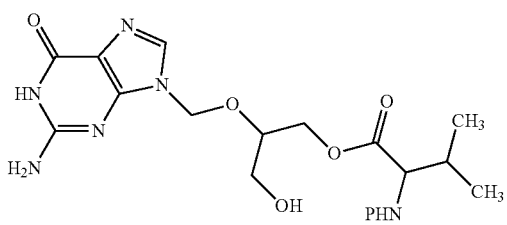

wherein P is an amino protecting group, in a suitable solvent provided that the suitable solvent is not methanol or ethanol.

A second aspect of present invention provides pure valganciclovir hydrochloride.

A third aspect of the present invention provides pure valganciclovir hydrochloride free of N-alkyl impurities by HPLC.

A fourth aspect of the present invention provides pure valganciclovir hydrochloride having less than about 0.25% total impurities by HPLC.

BRIEF DESCRIPTION OF THE DRAWINGS

FIG. 2A: Peak table corresponding to FIG. 2.

DETAILED DESCRIPTION OF THE INVENTION

Figure 1:
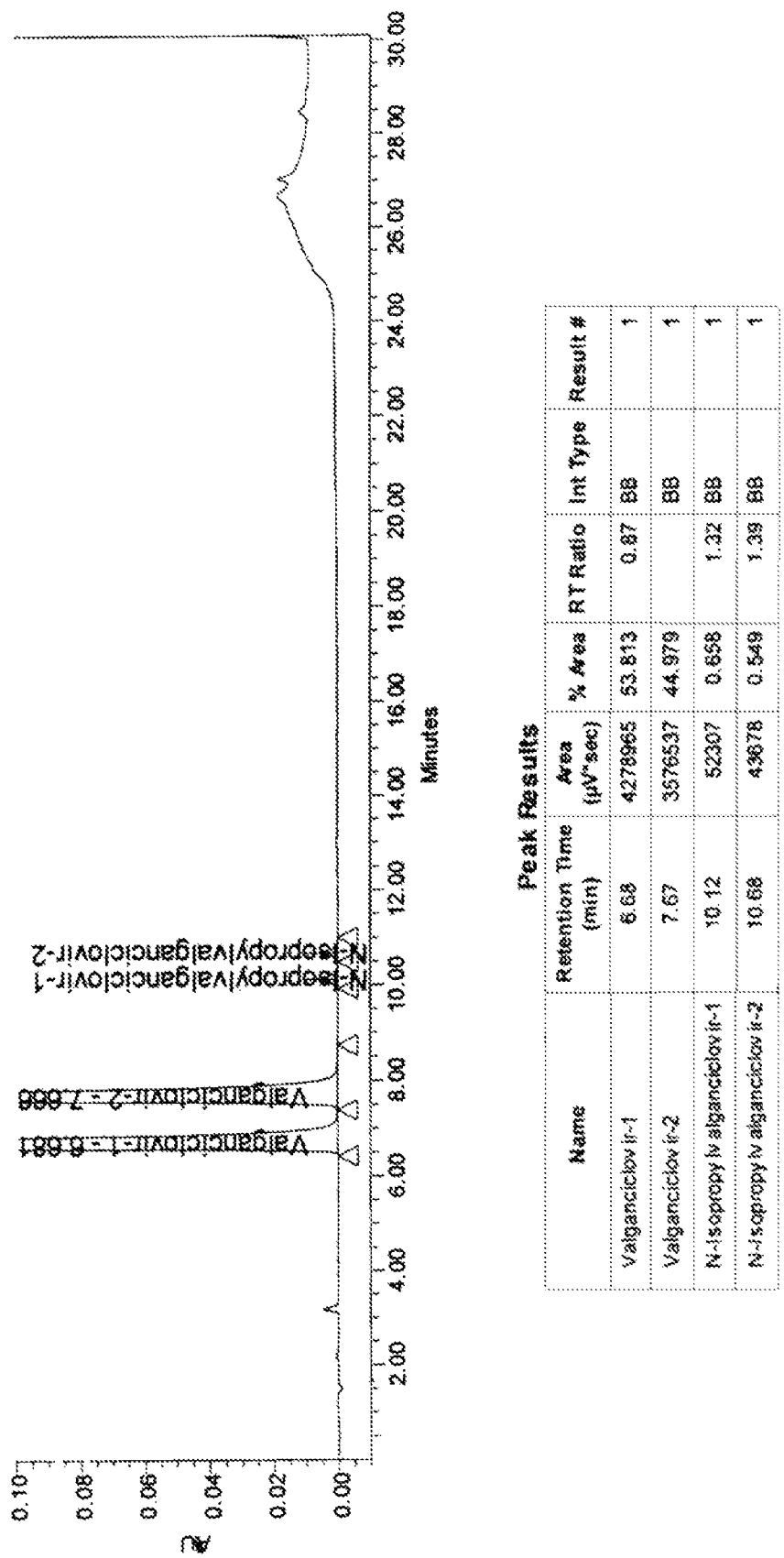
FIG. 1: HPLC chromatogram valganciclovir hydrochloride spiked with N-isopropyl impurity.

The term "amino protecting group", as used herein, means a chemical group that prevents an otherwise reactive amino group from participating in undesirable chemical reactions and which may be subsequently removed easily during downstream process steps when protection of the reactive amino group is no longer required. Amino protecting groups may be selected from benzyloxycarbonyl-L-valine, N-t-butoxycarbonyl valine, N-formyl valine, 9-fluorenylmethoxycarbonyl, trityl and the like. Preferably, benzyloxycarbonyl-L-valine may be used.

The term "valganciclovir hydrochloride", as used herein, includes anhydrous, hydrate and solvate forms thereof.

The term "pure valganciclovir hydrochloride", as used herein, means valganciclovir hydrochloride having less than about 0.1% of any single impurity by HPLC.

The term "any single impurity", as used herein, includes of ganciclovir, bis-valine ester analogue of ganciclovir, ganciclovir monopropionate, valganciclovir dimer, N-ethyl valganciclovir and N-methyl valganciclovir impurity.

The term "valganciclovir hydrochloride free of N-alkyl impurities", as used herein, means valganciclovir hydrochloride free of N-methyl valganciclovir, N-ethyl valganciclovir and N-isopropyl valganciclovir impurities.

Mono-protected ganciclovir of Formula IV, to be used for the preparation of valganciclovir hydrochloride of Formula I, can be prepared by the processes reported in the literature such as those described in U.S. Pat. Nos. 6,083,953; 6,340,756 and WO 2005/092891, which are incorporated herein by reference. The starting mono-protected ganciclovir of Formula IV can be obtained as a solution directly from a reaction mixture in which mono-protected ganciclovir is formed and used as such without isolation.

The deprotection of mono-protected ganciclovir of Formula IV may be carried out by hydrolysis or by hydrogenation, preferably by hydrogenation.

Hydrogenation may be carried out using a transition metal catalyst. The transition metal catalyst may be a supported transition metal catalyst or a salt of a transition metal. The supported transition metal catalyst may be selected from raney nickel, rhodium, ruthenium, platinum, palladium supported on carbon. The salts of transition metals may be selected from salts of platinum, rhodium and the like. Preferably, supported transition metal catalyst such as palladium supported on carbon may be used.

Hydrogenation may be carried out at a temperature of about 15° C. to about 70° C., preferably at about 25° C. to 45° C.

Hydrogenation may be carried out at a pressure of about 0.2-1.5 kg/cm$^3$, preferably at about 0.5-1 kg/cm$^3$.

Hydrogenation may be carried out for a period of about 30 minutes to about 2 hours, preferably for about 1 hour.

The suitable solvent to be used for the deprotection of mono-protected ganciclovir of Formula IV may be selected from $C_3$-$C_5$ alcohols, ketones, ethers, chlorinated hydrocarbons, esters, nitriles, amides or a mixture thereof. Examples of alcohols are n-propanol, iso-propanol, n-butanol, iso-butanol or sec-butanol. Examples of ketones are acetone, methyl ethyl ketone or methyl isobutyl ketone. Examples of ethers are diethyl ether, methyl tert-butyl ether, diisopropyl ether, tetrahydrofuran or dioxane. Examples of chlorinated hydrocarbons are chloroform, dichloromethane or 1,2-dichloroethane. Examples of esters are methyl acetate, ethyl acetate, propyl acetate or butyl acetate. Examples of nitrile may include acetonitrile or propionitrile. Examples of amides are N,N-dimethylformamide or N,N-dimethylacetamide. Preferably, alcohol such as iso-propanol may be used.

The suitable solvent may contain water. Preferably, about 15% to 40% aqueous alcohol such as iso-propanol may be used.

Isolation may be accomplished by concentration, precipitation, cooling, filtration or centrifugation, or a combination thereof followed by drying. Preferably, the reaction mass may be filtered.

The reaction mass may be further purified. Purification may be carried out by crystallization or by chromatography.

Crystallization may be carried out by adding a suitable solvent over a period of about 30 minutes to about 2 hours, preferably over a period of about 1 hour, at ambient temperature. The reaction mass may be cooled to −10° C. to +20° C., maintained for about 30 minutes to about 2 hours, filtered, washed with the suitable solvent and dried.

The process of the present invention provides pure valganciclovir hydrochloride.

Pure valganciclovir hydrochloride obtained by the process of the present invention may have less than about 0.1% of any single impurity by HPLC.

In one embodiment, pure valganciclovir hydrochloride obtained by the process of the present invention may have less than about 0.1% ganciclovir. In another embodiment pure valganciclovir hydrochloride obtained by the process of the present invention may have less than about 0.05% ganciclovir. In a preferred embodiment pure valganciclovir hydrochloride obtained by the process of the present invention may have about 0.03% ganciclovir.

In another embodiment, pure valganciclovir hydrochloride obtained by the process of the present invention may have less than about 0.1% bis-valine ester analogue of ganciclovir. In yet another embodiment, pure valganciclovir hydrochloride obtained by the process of the present invention may have less than about 0.05% bis-valine ester analogue of ganciclovir. In a preferred embodiment, pure valganciclovir hydrochloride obtained by the process of the present invention may be free of bis-valine ester analogue of ganciclovir.

In another embodiment, pure valganciclovir hydrochloride obtained by the process of the present invention may have less than about 0.1% ganciclovir monopropionate. In yet another embodiment, pure valganciclovir hydrochloride obtained by the process of the present invention may have less than about 0.05% ganciclovir monopropionate. In a preferred embodiment, pure valganciclovir hydrochloride obtained by the process of the present invention may have about 0.01% ganciclovir monopropionate.

In another embodiment, pure valganciclovir hydrochloride obtained by the process of the present invention may have less than about 0.1% valganciclovir dimer. In yet another embodiment, pure valganciclovir hydrochloride obtained by the process of the present invention may have less than about 0.05% valganciclovir dimer. In yet another embodiment, pure valganciclovir hydrochloride obtained by the process of the present invention may have less than about 0.01% valganciclovir dimer. In a preferred embodiment, pure valganciclovir hydrochloride obtained by the process of the present invention may be free of valganciclovir dimer.

The process of the present invention provides pure valganciclovir hydrochloride free of N-alkyl impurities.

In one embodiment, pure valganciclovir hydrochloride obtained by the process of the invention may have less than about 0.02% N-methyl valganciclovir. In another embodiment, pure valganciclovir hydrochloride obtained by the process of the invention may have less than about 0.01% N-methyl valganciclovir. In a preferred embodiment, pure valganciclovir hydrochloride obtained by the process of the invention may have about 0.007% N-methyl valganciclovir.

In another embodiment, pure valganciclovir hydrochloride obtained by the process of the invention may be free of N-ethyl valgancicolvir.

In yet another embodiment, pure valganciclovir hydrochloride obtained by the process of the invention may be free of N-isopropyl valganciclovir.

Valganciclovir hydrochloride free of bis-valine ester analogue of ganciclovir, valganciclovir dimer or N-ethyl valganciclovir as used herein means valganciclovir hydrochloride having no detectable amount of bis-valine ester analogue of ganciclovir, valganciclovir dimer or N-methyl valganciclovir.

The process of the present invention provides pure valganciclovir hydrochloride having less than about 0.25% total impurities by HPLC.

In a preferred embodiment, the present invention provides pure valganciclovir hydrochloride having less than about 0.21% total impurities by HPLC.

Valganciclovir hydrochloride prepared by the process of the present invention may be converted into amorphous form by conventional methods such as spray drying.

In the foregoing section, embodiments are described by way of examples to illustrate the process of invention. However, this is not intended in any way to limit the scope of the present invention. Several variants of the examples would be evident to persons ordinarily skilled in the art which are within the scope of the present invention.

HPLC Method for Determining Chromatographic Purity

Zorbax SBC18 (150×4.6 mm), 3.5 μm
Eluent: Buffer pH 2.8/methanol
Temperature: 25° C. to 30° C.
Flow rate: 1.0 mL/minute

EXAMPLES

Comparative Examples

Example 1

Preparation of Valganciclovir Hydrochloride Using Methanol

Hydrochloric acid (2.6 g) and 10% palladium on carbon (1.1 g, 50% wet) were added to a solution of mono-benzyloxycarbonyl-L-valine ganciclovir (10 g) in aqueous methanol (Methanol:Water::50 mL:8 mL) at ambient temperature. The reaction mass was flushed with nitrogen twice and hydrogenated at about 35° C. to 40° C. at hydrogen pressure of about 0.5-1 kg/cm² for about 1 hour. The reaction mass was filtered and washed with methanol (10 mL). Methanol was distilled out completely under reduced pressure at about 30° C. to 35° C. The residue was dissolved in water (8 mL) and stirred to obtain clear solution. Iso-propanol (56 mL) was added slowly over a period of about 1 hour. The reaction mass was cooled to about 0 to 5° C., maintained for about 1 hour, filtered, washed with 10% aqueous iso-propanol (10 mL) followed by washing with iso-propanol (10 mL) and dried to obtain valganciclovir hydrochloride (6 g).
Yield: 75%
HPLC Purity: 98.48%
N-methyl valganciclovir: 0.02% (by HPLC)
Total unknown impurities: 0.539 (by HPLC)
Total impurities: 0.973 (by HPLC)

Example 2

Preparation of Valganciclovir Hydrochloride Using Ethanol

Hydrochloric acid (2.6 g) and 10% palladium on carbon (1.1 g, 50% wet) were added to a solution of mono-benzyloxycarbonyl-L-valine ganciclovir (10 g) in aqueous ethanol (Ethanol:Water::96 mL:26 mL) at ambient temperature. The reaction mass was flushed with nitrogen twice and hydrogenated at about 35° C. to 40° C. under a hydrogen pressure of about 0.5-1 kg/cm² for about 1 hour. The reaction mass was filtered and washed with 10% aqueous ethanol (10 mL). Ethanol was distilled out completely under reduced pressure at about 30° C. to 35° C. The residue was dissolved in water (6.25 mL) and stirred to obtain clear solution. Iso-propanol (56 mL) was added slowly over a period of about 1 hour. The reaction mass was cooled to about 10° C. to 15° C., maintained for about 1 hour, filtered, washed with 10% aqueous iso-propanol (10 mL) followed by washing with iso-propanol (10 mL) and dried to obtain valganciclovir hydrochloride (5.8 g).
Yield: 72.5%
HPLC Purity: 98.41%
N-ethyl valganciclovir: 0.027% (by HPLC)
Total unknown impurities: 0.591 (by HPLC)
Total impurities: 0.994 (by HPLC)

Working Examples

Example 1

Preparation of Valganciclovir Hydrochloride Using Iso-Propanol

Hydrochloric acid (13 g) and 10% palladium on carbon (5.5 g) was added to a solution of mono-benzyloxycarbonyl-L-valine ganciclovir (50 g) in 23% aqueous iso-propanol (Iso-propanol:water::500 mL:150 mL). The reaction mixture was hydrogenated at about 25° C. to 40° C. under hydrogen pressure of 0.5-1 kg/cm² for about 1 hour. After completion of the reaction, the reaction mass was filtered and washed with iso-propanol:water mixture (Iso-propanol:water::45 mL:5 mL). Iso-propanol (500 mL) was added over a period of about 1 hour. The reaction mass was cooled to 0° C., maintained at about 0° C. to about −5° C. for about 1 hour, filtered, washed with 10% aqueous iso-propanol solution (50 mL) followed by washing with iso-propanol (50 mL) and dried to obtain valganciclovir hydrochloride (31 g).
Yield: 77.5%
HPLC Purity: 99.65%
Total unknown impurities: 0.134
Total impurities: 0.216

Example 2

Preparation of Valganciclovir Hydrochloride Using Iso-Propanol

Hydrochloric acid (2.08 g) and 10% palladium on carbon (0.88 g, 50% wet) was added to a solution of mono-benzyloxycarbonyl-L-valine ganciclovir (8 g) in 30% aqueous iso-propanol (Iso-propanol:Water::64 mL:28 mL). The reaction mixture was flushed with nitrogen twice and hydrogenated at 35° C. to 40° C. under hydrogen pressure of 0.5-1 Kg/cm$^2$ for about 1 hour. After completion of the reaction, the reaction mass was filtered and washed with 20% aqueous iso-propanol (Iso-propanol:Water::6.4 mL:1.6 mL). Iso-propanol (123.3 mL) was added at about 20° C. to 25° C. in about 1 hour. The reaction mass was cooled to about 10° C. to 15° C. and maintained for about 1 hour, filtered, washed with 10% aqueous iso-propanol solution (10 mL) followed by washing with iso-propanol (10 mL) and dried to obtain valganciclovir hydrochloride (4.8 g).

Yield: 75%
HPLC Purity: 99.66%
Total Unknown impurities: 0.127
Total impurities: 0.212

Figure 2:
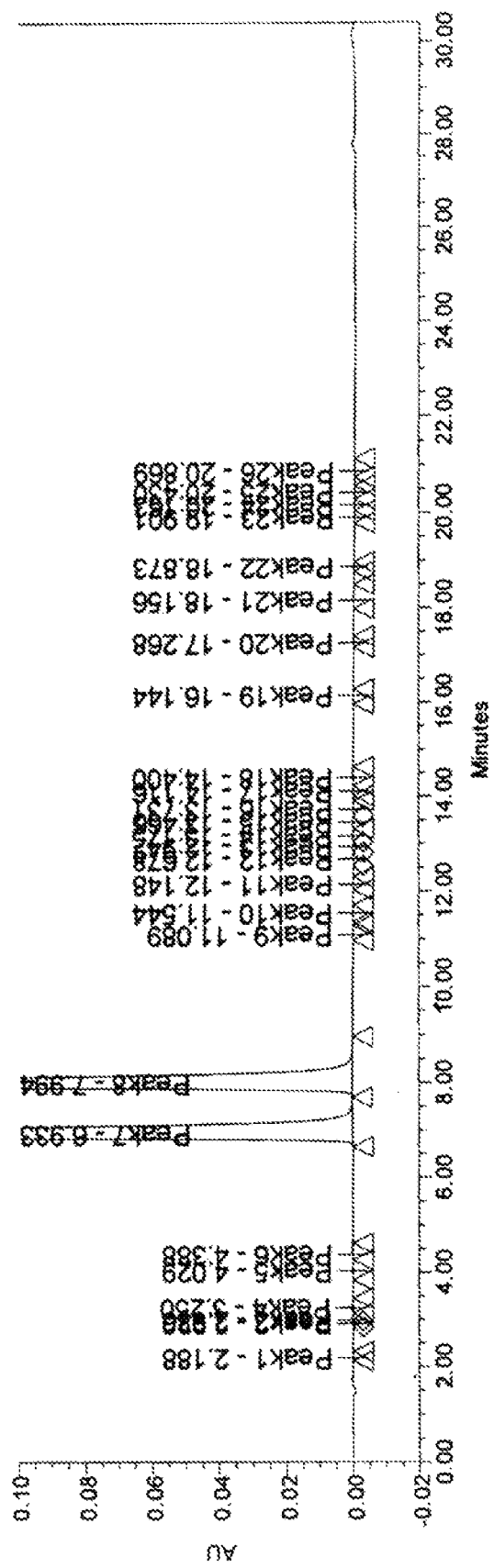
FIG. 2: HPLC chromatogram of valganciclovir hydrochloride prepared by the process of the present invention.

The HPLC chromatogram is as shown in FIG. 2.

We claim:

1. A process for the preparation of valganciclovir hydrochloride of Formula I having less than 0.1% of any single impurity selected from ganciclovir, a bis-valine ester analogue of ganciclovir, ganciclovir monopropionate, valganciclovir dimer, N-ethyl valganciclovir, and N-methyl valganciclovir, as determined by HPLC,

FORMULA I

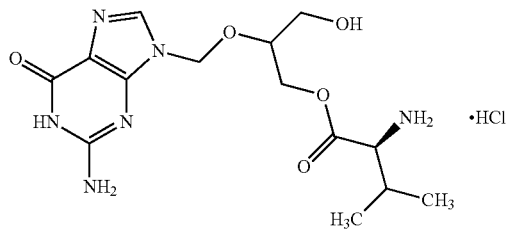

comprising deprotection of mono-protected ganciclovir of Formula IV

FORMULA IV

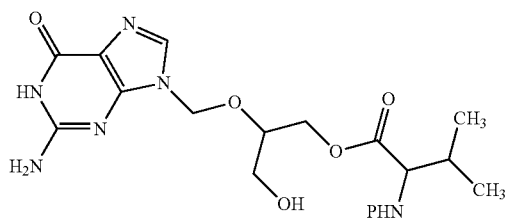

wherein P is an amino protecting group, in a suitable solvent containing 15% to 40% water, provided that the suitable solvent is not methanol or ethanol.

2. The process according to claim 1, wherein mono-protected ganciclovir of Formula IV, obtained as a solution directly from a reaction mixture in which mono-protected ganciclovir of Formula IV is formed, is used as such without isolation.

3. The process according to claim 1, wherein the deprotection is carried out by hydrogenation.

4. The process according to claim 1, wherein the deprotection is carried out by hydrolysis.

5. The process according to claim 3, wherein the hydrogenation is carried out using a transition metal catalyst selected from a supported transition metal catalyst or salt of a transition metal.

6. The process according to claim 5, wherein the supported transition metal catalyst is selected from raney nickel, rhodium, ruthenium, platinum, or palladium supported on carbon.

7. The process according to claim 1, wherein the suitable solvent is selected from the group comprising of alcohols, ketones, ethers, chlorinated hydrocarbons, esters, nitriles, amides or mixtures thereof.

8. The process according to claim 7, wherein the alcohol is selected from the group comprising of n-propanol, iso-propanol, n-butanol, iso-butanol or sec-butanol.

9. The process according to claim 8, wherein the alcohol is iso-propanol.

10. The process according to claim 9, wherein the alcohol is aqueous iso-propanol.

11. The valganciclovir hydrochloride of Formula I having less than 0.1% of any single impurity selected from ganciclovir, a bis-valine ester analogue of ganciclovir, ganciclovir monopropionate, valganciclovir dimer, N-ethyl valganciclovir, and N-methyl valganciclovir, as determined by

FORMULA I

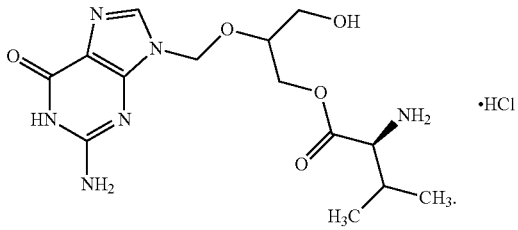

HPLC.

12. The valganciclovir hydrochloride of claim 11 free of N-alkyl impurities as determined by HPLC.

13. The valganciclovir hydrochloride of claim 11 having less than 0.25% of total impurities as determined by HPLC.

* * * * *